United States Patent [19]

Aslanian et al.

[11] 4,361,147
[45] Nov. 30, 1982

[54] FLOW CONTROL DEVICE FOR ADMINISTRATION OF INTRAVENOUS FLUIDS

[75] Inventors: Jerry L. Aslanian, Phoenix; Jody L. Numbers, Scottsdale, both of Ariz.

[73] Assignee: Master Medical Corporation, Phoenix, Ariz.

[21] Appl. No.: 209,604

[22] Filed: Nov. 24, 1980

Related U.S. Application Data

[63] Continuation-in-part of Ser. No. 5,313, Jan. 22, 1979, Pat. No. 4,294,246.

[51] Int. Cl.³ .............................................. A61M 5/00
[52] U.S. Cl. ................................................. 128/214 E
[58] Field of Search ............ 128/214 E, 214 R, 214.2, 128/214.4, 214 C, 274; 251/203, 205

[56] References Cited

U.S. PATENT DOCUMENTS

| | | | |
|---|---|---|---|
| 2,980,392 | 4/1961 | Greenwood | 251/205 |
| 3,384,338 | 5/1968 | Dermody | 251/205 |
| 3,408,040 | 10/1968 | Kraft | 251/203 |
| 3,410,521 | 11/1968 | Sowers et al. | 251/205 |
| 3,785,378 | 1/1974 | Stewart | 128/214 C |

Primary Examiner—Richard J. Apley
Assistant Examiner—T. J. Wallen
Attorney, Agent, or Firm—Gregory J. Nelson

[57] ABSTRACT

A metering apparatus and system for controlling the administration of intravenous fluids (IV) having a flow passage within a housing connectable to a source of IV fluid and to a delivery tube terminating at an administration needle. In the metering apparatus, a metering pin is axially moveable within the passage and relative to a valve seat and defines a flow passageway and a variable area flow notch which are positionable relative to the valve seat to regulate flow from a purge to a flow blocking position. In the preferred embodiment, positioning of the metering pin is accomplished by a cam engaging a portion of the pin forming a cam follower. The cam is manually adjustable by a dial on the device to accomplish accurate, repeatable and continuous flow adjustment over the full range. The system incorporates the metering apparatus, a source of IV fluid, a drip chamber and administration means.

7 Claims, 29 Drawing Figures

FLOW CONTROL DEVICE FOR ADMINISTRATION OF INTRAVENOUS FLUIDS

The present application is a continuation-in-part application of Ser. No. 5,313 filed Jan. 22, 1979 entitled "FLOW CONTROL DEVICE FOR ADMINISTRATION OF IV FLUIDS", now U.S. Pat. No. 4,294,246.

The present invention relates to a device for regulator controlling the flow of intravenous (IV) or parenteral fluids. More particularly, the present invention relates to a flow metering device for precisely establishing and maintaining a preselected flow rate during the administration of IV liquids at the patient.

The administration of fluids by intravenous infusion is a common medical procedure. Representative intravenous fluids include blood, plasma, dextrose and isotonic saline solutions. IV infusions are generally carried out with the container of IV fluid suspended above the patient. Customarily such containers have a seal which is broken by the insertion of a piercer or "spike" and the fluid is delivered to the patient at an administration needle through a drip chamber and flexible tubing connected to the container at the spike. The purpose of the drip chamber is to facilitate the determination of the flow or drip rate through the tubing. The infusion rate is generally varied or regulated by use of a pinch valve or roller clamp associated with the tubing.

Initially when infusions are carried out, the tubing and needle are initially purged of air by initiating a flow of fluid through the tubing. The needle is then inserted into a vena puncture site at a suitable location such as one of the veins in the wrist area and infusion is initiated. Preferably, when the vena puncture occurs in the lower arm of the patient, the arm should be properly stabilized in a contoured IV arm support. Medical personnel administering the IV will close the pinch valve or roller clamp to restrict the IV tubing and the number of drops passing through the drip tube are counted. The appropriate flow rate is established by trial and error method by progressively restricting or opening the tubing by means of the pinch valve.

The administration procedure described requires the attention of the nurse or physician for a substantial time. The time is required not only in the initial establishment of the proper flow rate but continual monitoring is required. It is the general practice of many medical facilities to require a nurse or physician to periodically check the flow rate by counting drops at the drop chamber. In addition to the procedure requiring substantial time, the method of regulating flow by means of a manual clamp secured to the drip tubing is extremely inaccurate. Temperature changes will cause expansions and contractions of the IV tubing permitting the flow rate to vary. Tubing may lose "memory" and collapse under continuous squeezing necessitating constant re-adjustments of the initial setting. Roller clamps or pinch valves of the type described have a tendency to slip off which can in some cases be extremely dangerous to the patient. If an inadvertant and sudden increase in flow of IV fluid is encountered, the patient can go into "speed shock". Obviously, flow decreases are similarly undesirable in treating a patient. Some independent tests have shown that conventional pinch valves and roller clamps maintain flow only within about 25% accuracy thereby requiring constant re-adjustment. It will be appreciated that controlling infusion rates to the desired degree of accuracy by conventional pinch valves and roller clamps is extremely difficult even with constant attention on the part of attending medical personnel.

Various expedients have been resorted to in an effort to correct the problem set forth above. Flow regulating devices of various types have been developed and can be found in the prior art. For example, U.S. Pat. No. 3,785,378 to Stewart shows a valve for the administration of intravenous fluids which has an annular member forming a central passage through which fluid is flowable to an end face with multiple grooves. The inner ends of the grooves communicate with the passage and a flow control member is rotatable to place a flow port successively and selectively in communication with the grooves to vary the flow rate.

Another approach to the problem is found in U.S. Pat. No. 3,877,428 to Seagle et al. which shows an infusion control device for selectively controlling the rate of administration of fluids parenterally to a patient. The control device is attachable along the IV tube and includes a rotatable metering place defining a capillary flow path between the input and the output of the control device. A metering plate is axially rotatable with respect to the input and output ports to vary the effective length of the flow path so as to regulate flow between full flow and zero flow conditions.

A somewhat similar approach is shown in U.S. Pat. No. 3,880,401 which discloses a flow metering valve having inner and outer component parts which are movable relative one to another at screw threads to effect relative axial movement of a metering valve plug in and out of a metering bore for regulating and terminating flow through the valve flow passage.

While all of the aforementioned devices are substantial improvements over the roller clamp or pinch valve type of arrangement traditionally used, these devices impose certain problems. The prior art devices, due to their construction, present problems in manufacture making them impractical in many instances. Devices of the aforementioned type generally require the attending nurse or physician to operate the device with both hands which is often awkward and may therefore require two medical personnel in attendance for set-up and purge procedures. Further, these devices do not always provide the constancy and repeatability of flow rates desired by medical personnel.

Briefly, the present invention overcomes the problems and provides a novel infusion control device which can be adjusted to maintain various settings from zero to full flow conditions with repeatability. The invention provides precise and continuous and infinite variable control over the flow of fluid. The flow rate may be changed by the attendant by simply moving a control member, an operation which may be performed with one hand. Briefly, in the preferred embodiment, the flow control device of the present invention comprises a housing which contains an axially extending sleeve. A metering tube including a valve seat portion, is received within the sleeve and defines a fluid passageway. A metering pin is axially moveable relative to the seat and is provided with a flow passageway including a variable area notch. One end of the sleeve is connectable to a drip chamber and the lower end of the tube terminates in a male coupling or nipple which is attachable to IV tubing. Flow adjusting means serve to position the metering pin relative to the valve to adjust fluid flow through the flow passageway. In the preferred embodiment of the invention, the flow adjustment means comprises a cam which cooperates with a follower on the metering pin. The cam is rotated by means of a dial exteriorly of the valve housing. In other embodiments, the flow adjusting means may comprise a rack and pinion or plunger mechanism operatively connected to the metering pin.

The above and other objects and advantages of the present invention will become more readily apparent from the following description, claims and drawings in which:

Figure 1:
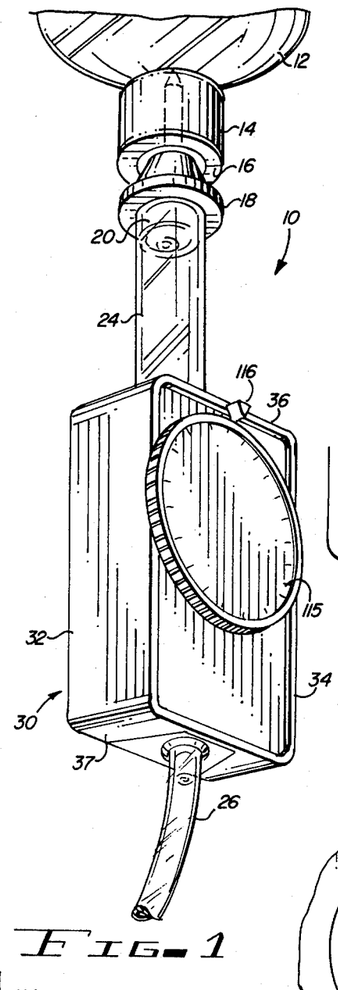
FIG. 1 is a perspective view of the flow regulating device of the present invention shown in position connected to an IV bottle.

Turning now to the drawings, FIG. 1 generally shows the flow control device of the present invention which is designated by the numeral 10. Flow control device 10 is shown connected in an IV system including a bottle or container 12 of an appropriate IV solution such as plasma, blood, dextrose or saline solution. Bottle 12 terminates at an outlet 14 which is sealed by a plug or stopper 16. A piercing spike 18 is inserted through the stopper or closure 16 which has cylindrical projection 20 which receives drip chamber 24. Various IV systems conventionally may be open or closed. In some cases the spike or piercer 18 may be vented through an appropriate filter media to admit air into the bottle 12. The flow regulating device 10 of the present invention is shown interposed between the drip chamber 24 and IV tubing 26 which terminates at an IV administration tip or needle, not shown.

The details of construction of the IV control device 10 are best seen in FIGS. 2 through 7. Control device 10 includes a generally rectangular body or housing 30 having opposite side walls 32 and 34 and top and bottom 36 and 37, respectively.

Figure 2:
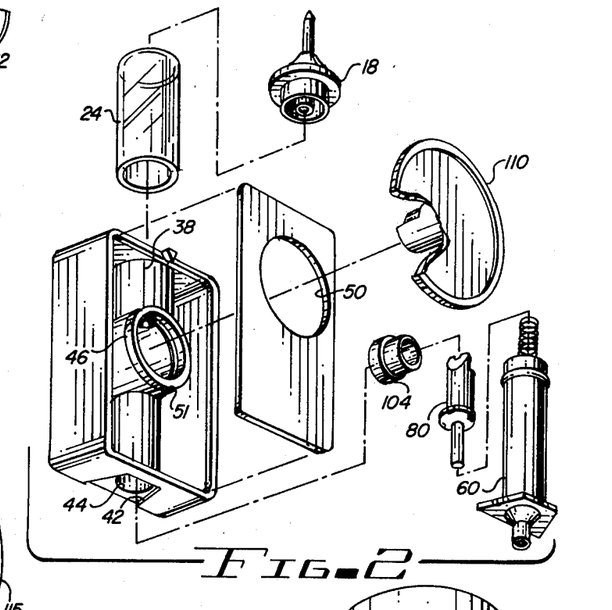
FIG. 2 is an exploded perspective view of the flow regulating device of the present invention.

A channel 38 having a cylindrical bore 44 extends axially between top and bottom walls 36 and 37 and opens at the top and bottom walls. Drip chamber 24 is connectable at the top end of channel 38 at top wall 36 at an appropriate fitting. A recess 42 is provided in bottom wall 37 extending about bore 44.

An annular hub 46 intercepts cylindrical channel 38 intermediate end walls 36 and 37 dividing the channel into upper and lower sections. Cover plate 48, which is generally rectangular in configuration, is positionable over the face of the housing 48 engaging the edges of the side and end walls. Plate 48 is provided with a circular cut-out 50 receiving the upper edge of hub 46. Plate 48 can be secured in place by any convenient means such as by mechanical fastening means or adhesive bonding. A projection 51 which serves as a stop, as will be more fully explained, extends from hub 51.

Metering tube 60 is inserted in the lower portion of cylindrical channel 38 and has an upper edge 61 and terminates in channel 38 at a location below hub 46. Metering tube 60 defines an interior cylindrical bore 64.

The lower end of metering tube 60 terminates at a nipple or coupling 66 which is connectable to IV tubing 26. Coupling or nipple 66 defines an axial passageway 68 which communicates with bore 64. Passage 68 is of smaller diameter than bore 64 so that an annular surface 70 is defined at the lower end of bore 64. A generally trapezoidal flange 72 projects from the lower end of tube 60 corresponding and shaped to configuration of recess 44.

Figure 9:
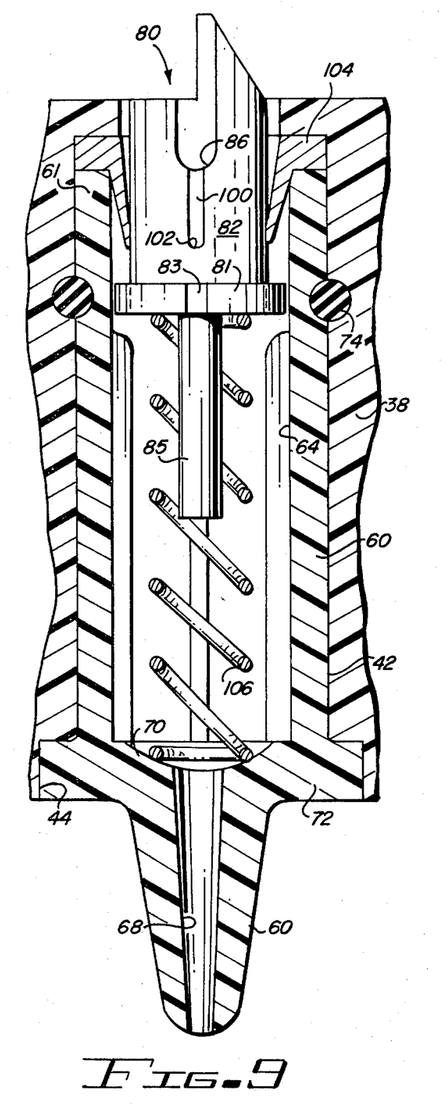
FIG. 9 is a view, partly in section, illustrating the metering tube and pin assembly.

Annular sealing member 74 is integrally formed or is placed about tube 60 and, as best seen in FIG. 9, forms a fluid or hydrostatic seal between the exterior of the metering tube 60 and the interior of cylindrical channel 38.

Metering or control of flow is achieved by axial displacement of metering pin 80 relative to valve seat 104. Pin 80 is best shown in FIGS. 5 to 8. Metering pin 80 has a generally cylindrical body 82 which terminates at upper end at a projection 88. Projection 88 defines a cam follower surface as will be more fully described. A circular flange 81 projects from the lower end of body 82 and is provided with a series of peripheral flow grooves 83. The diameter of the circular flange 81 closely corresponds to the inner diameter of metering tube 60 and is selected to permit metering pin 80 to slide axially within the tube. A guide pin 85 extends axially from flange 81.

Figure 6:
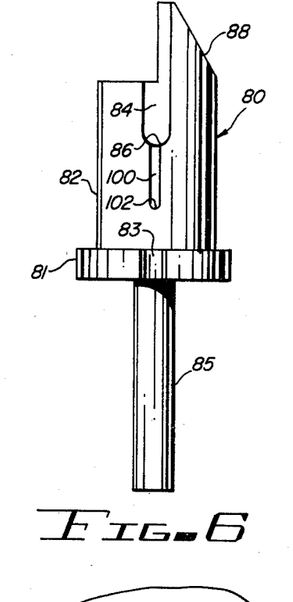
FIG. 6 is an elevational view of the metering pin showing the flow passageway.
Figure 7:
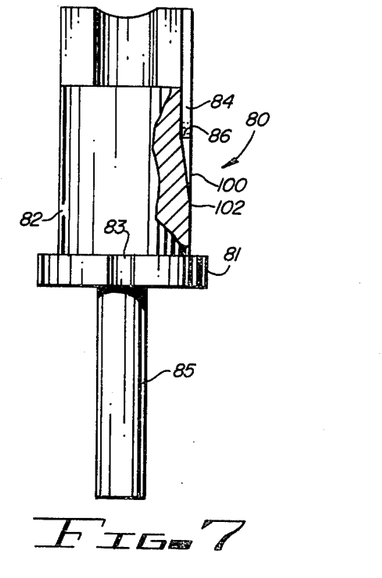
FIG. 7 is a front elevational view of the metering pin.
Figure 8:
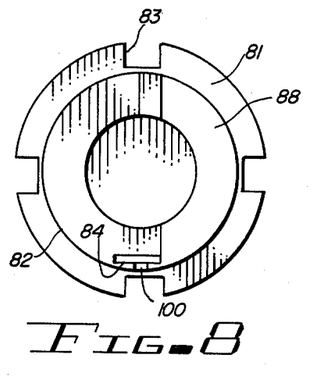
FIG. 8 is a top view of the metering pin.

Flow through the device is directed along flow passage 84 which extends axially along the outer surface of body 82 terminating at lower end wall 86 at an intermediate location. The cross-sectional configuration of the flow passage 84 may vary but the passage is shown as having a flat bottom and spaced apart vertical side walls with the width of the passage being several times the depth. A metering notch 100 communicates with flow passage 82 at end wall 86. Metering notch 100 preferably decreases or tapers in cross-sectional area having a maximum cross-sectional area at its upper end where the notch intercepts end wall 86 and diminishes or decreases in area downwardly terminating at end 102 at a location above flange 81. The notch 100 may be of various cross-sectional shapes but is shown as being configured to decrease in depth axially proceeding towards flange 81. Notch 100 may also be of uniform depth having a decreasing width or, in some cases, may decrease in both width and depth. It is also possible to reverse the orientation of the flow passage and metering notch with the direction of operation being accordingly reversed.

Valve seat 104 is shown as a cylindrical insert which cooperatively fits into a recess provided at the upper end of metering tube or sleeve 60. Valve seat 104 is provided with a bore 94 having lower edge 111 which forms a valving surface which cooperates with metering pin 80 to regulate or meter flow through the control device. Valve seat 104 is held in place in sleeve or tube 60 by annular shoulder 105.

In an assembled position, as seen in FIG. 9, metering pin 80 is slideably received within bore 64 of tube 62. Tube 62 is in turn, positioned in the lower portion of channel 38. A biasing compression spring 106 extends from end 70 of the bore 64 at the bottom of the metering tube and engages the underside of flange or disc 81 of metering pin 80 extending circumferentially about axial pin 85. Spring 106 urges or biases the metering pin upwardly placing the cam follower 88 in contact with cam 110.

Figure 3:
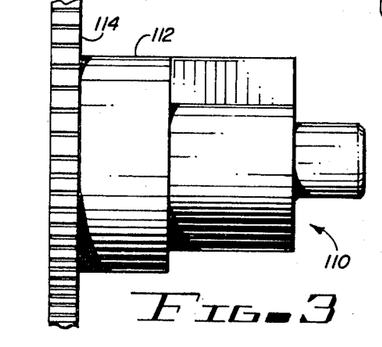
FIG. 3 is a side elevational view of the cam shown in FIG. 2.
Figures 4, 5:
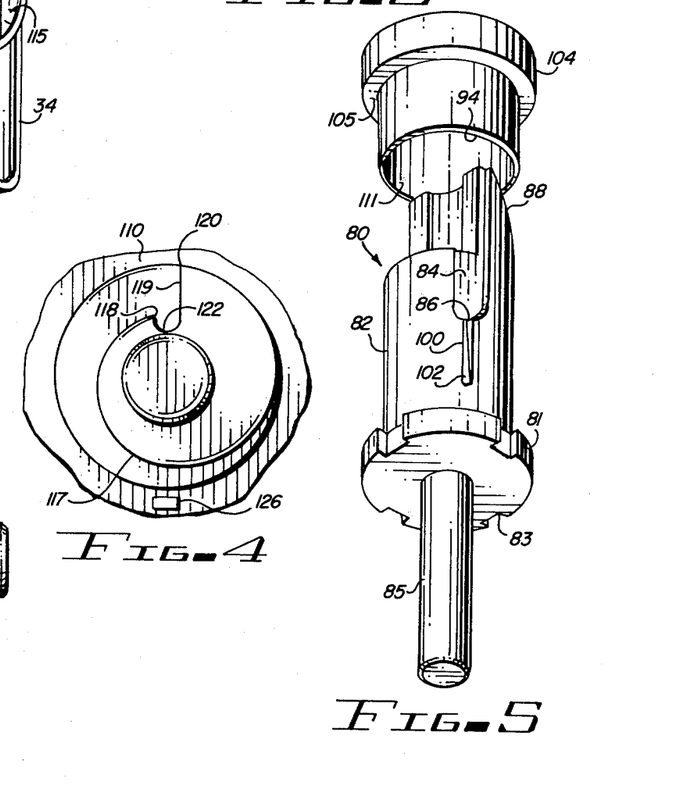
FIG. 4 is a plan view of the cam surface.
FIG. 5 is an enlarged perspective view of the metering pin and associated valve seat.

Cam 110 is best shown in FIGS. 3 and 4 and includes a cylindrical hub 112 which is rotatably received within hub 46 of housing 30. A circular dial 114 is secured to cylindrical journal 112 and is positioned at the face of the unit 10. Preferably the peripheral edges of dial 114 are serrated for improved gripping characteristics. As shown in FIG. 1, dial 114 also extends laterally beyond the opposite side walls 32 and 34 of the dial housing to facilitate manipulation of the dial with one hand. The outer surface of dial 114 is suitably graduated or calibrated with numerical or other indicia 115 to indicate appropriate flow rates. The calibrations are cooperatively read in conjunction with pointer 116 centrally positioned on the face of the housing at the front edge of top wall 36.

Cam 110 includes a cam surface 117 which is generally spiral on configuration extending from low point 118 through rise 119 to high point 120. A lug or projection 126 is provided on the inner face of the dial 114 and is engageable with projection 51 on hub 46 to restrict the rotation of the cam in both directions of rotation. Notch 122 is provided in the cam surface intermediate points 118 and 120 and will engage follower 88 of the metering pin in the "off" position.

The various components described above are assembled in a manner as best seen in FIGS. 2, 5 and 9 with the metering pin inserted in the lower portion of cylindrical channel 38 in the housing 30. The metering pin is slideable within bore 64 of sleeve 62 with flange 81 engaging the bore 64. The upper end of the metering tube is received within valve seat 104. The cam assembly 110 is positioned within the housing, the journal being rotatable within hub 46 and sealed by elastomeric O-ring 125.

Figures 9A, 9B, 9C:
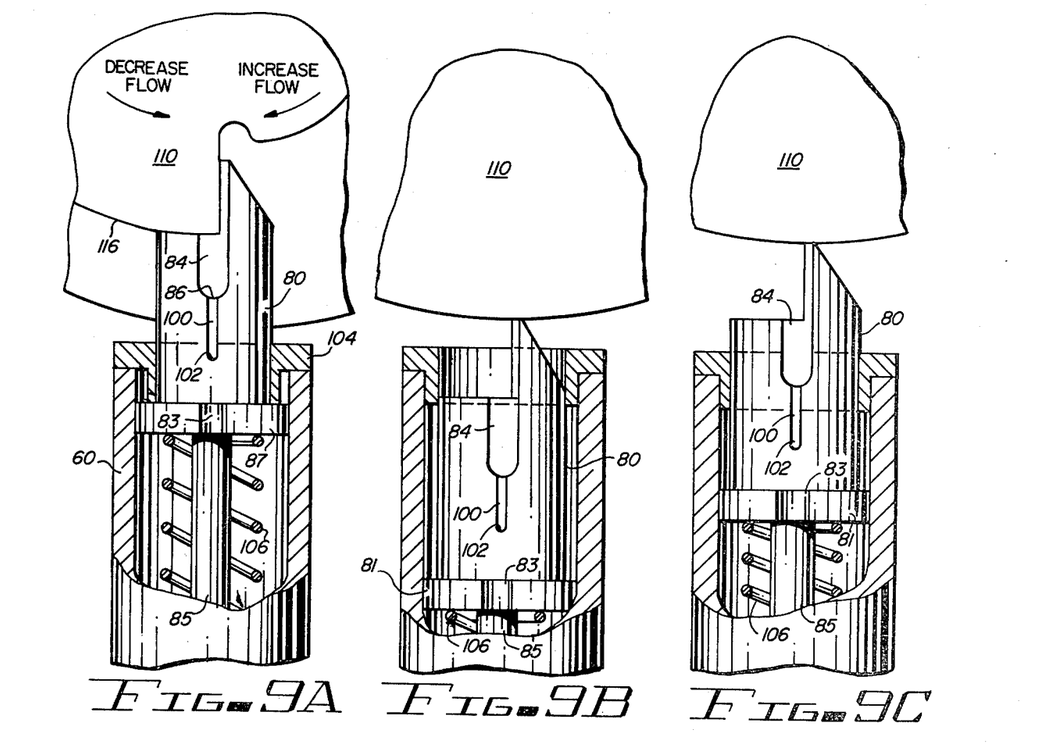
FIG. 9A is a partial sectional view illustrating the flow regulating device with the metering pin in a flow blocking position.
FIG. 9B is a partial sectional view of the device in a metering or flow controlling position.
FIG. 9C is a partial sectional view of the device in a metering or flow controlling position.

FIGS. 9A, 9B and 9C best illustrate the relative position of the metering pin and cam in various operating positions from a stop to a purge position. These figures are viewed from the face or front of the device 10 with the cam illustrated in dotted lines for convenience. As is shown in FIG. 1, the control device 10 is first connected in an IV system to a drip chamber 24 terminating at a spike or piercing device 18 which is inserted into the stopper 16 of a container or bottle containing an appropriate IV solution. The IV tubing 24 terminates at an administration tip and connected to the control device 10 at coupling 66. Generally dial 114 will be positioned in the "off" position with the appropriate indicia 115 aligned with marker or pointer 116. In this position, the stop or projection 126 on the inner surface of the dial 126 engages the cooperative projection at 51 on hub 46 so that further counter clockwise rotation as viewed in FIG. 9A is restricted. Cam follower 88 is engaged in cam notch 122. In the position shown in FIG. 9A, all flow through the device is stopped. Fluid entering the control device 10 through drip chamber 24 flows through upper delivery tube 38 where it will be blocked by the outer diameter of pin 80 and seat 104.

Prior to attaching the needle to the tubes, the attendant will rotate dial 114 clockwise until pointer 116 aligns with indicia 115 indicating a purge position. Rotation of dial 114 will, in turn, rotate the cam surface 116 clockwise as viewed in FIGS. 9A through 9C to axially depress the metering pin 80 against the force of spring 106. Metering pin 80 will be displaced to the position shown in FIG. 9B which positions the lower end 86 of flow passageway 84 below the lower edge of valve seat 104. This permits flow in upper delivery section of channel 38 to flow or bridge the valve seat through the larger area flow passageway and across slot 83 in flange 81. The flow is then directed to the lower end of the valve tube 60, through the IV tubing 24 to the administration tip. The purge condition is generally maintained for a brief period of time (approximately 30 cc fluid is usual recommended quantity to purge through system) so that all air is purged from the system prior to infusion. Dial 114 will then be returned to the off position shown in FIG. 9A which allows the metering pin to move axially upwardly terminating flow through the unit.

The needle can then be inserted into the patient at the vena puncture site and the needle attached to the tubing at a hub or fitting. Dial 114 is then rotated until the appropriate flow rate is achieved. In the delivery or metering position as shown in FIGS. 9C, the variable metering notch 100 may be variously positioned with respect to the lower edge 111 of the valve seat 104. Accordingly, the metering notch provides for progressive and almost infinite selection of flow rates from full on to off depending on the relative position of the metering notch and the lower edge 110 of the valve seat. For example, as the lower end 102 of the metering notch 100 approaches lower edge 111 of the valve seat, flow is progressively restricted. As more of the metering notch 100 is extended below edge 110, the flow rate increases. Thus, accurate flow rates can be precisely delivered with determinable repeatability by selective positioning of the metering pin by means of the dial and cam assembly. Flow rates can be stopped, decreased or increased selectively by rotation of the dial and cam assembly.

Thus, the successive and selective registration of the metering pin and valve seat contributes to the desired predeterminable flow rate function of the valve. The particular configuration of the metering notch and groove may vary as pointed out above, it being only necessary to have a substantially unrestricted section and a section of varying area. With the particular arrangement shown, the desired flow rate can be achieved reducing the risk of inaccurate fluid drip rate administration to the patient.

It is noted that the construction shown herein has a unique safety feature which prevents the unit from delivering IV fluid at a rate greater than the selected rate therefore minimizing the risk of infusing the patient with fluid at an excessive rate which can cause speed shock and can be extremely dangerous to the patient. Note that if the cam as shown in FIGS. 1 to 9 is set at a predetermined rate, the biasing spring 106 always urges the metering pin 80 upwardly into contact with the cam surface 117. This means that the biasing spring continually biases the metering pin towards the closed position and in the event of some malfunction, metering pin 80 will be urged upwardly to a decreased or off position so that the unit cannot deliver at a rate greater than the preset or established rate.

Another significant safety feature of the present invention is that the device allows the administrator of the IV a reference point for checking accuracy of flow rates to the patient. Once the dial is set, a pre-determined flow can be expected. If that flow rate is not achieved, as determined by a visual count, then the attendant should check for any problems such as blocked or crimped tubing and correct needle position in the vein. Improper needle position may occlude the cannula and impede flow temporarily. A change of position by the patient can result in a sudden flow increase when the occlusion is removed. With the device of the present invention, the attendant should be able to detect and remedy any such positional problems reducing danger of inaccurate infusion rates to the patient.

Figures 10, 11, 12, 13, 14, 15:
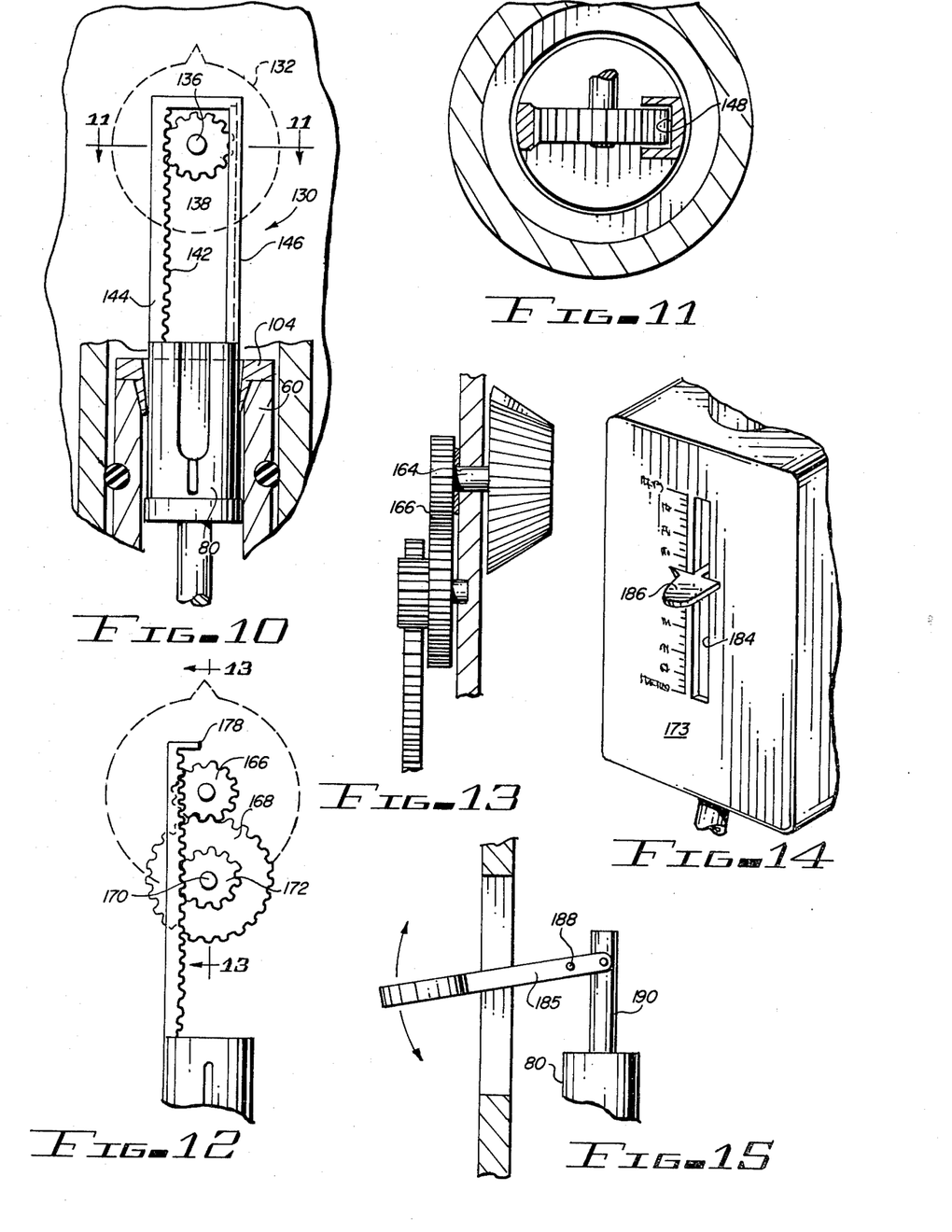
FIG. 10 is a side elevational view showing a rack and pinion for adjusting the position of the metering pin.
FIG. 11 is a sectional view taken along lines 11—11 of FIG. 10.
FIG. 12 is a side view showing adjustment means connected to the metering pin in the form of a gear reduction system.
FIG. 13 is a sectional view taken along lines 13—13 of FIG. 12.
FIG. 14 is a perspective view of still another embodiment of the control device of the present invention.
FIG. 15 is a partial side elevational view showing still another form of the metering pin adjustment means used with the embodiment shown in FIG. 14.
Figure 16:
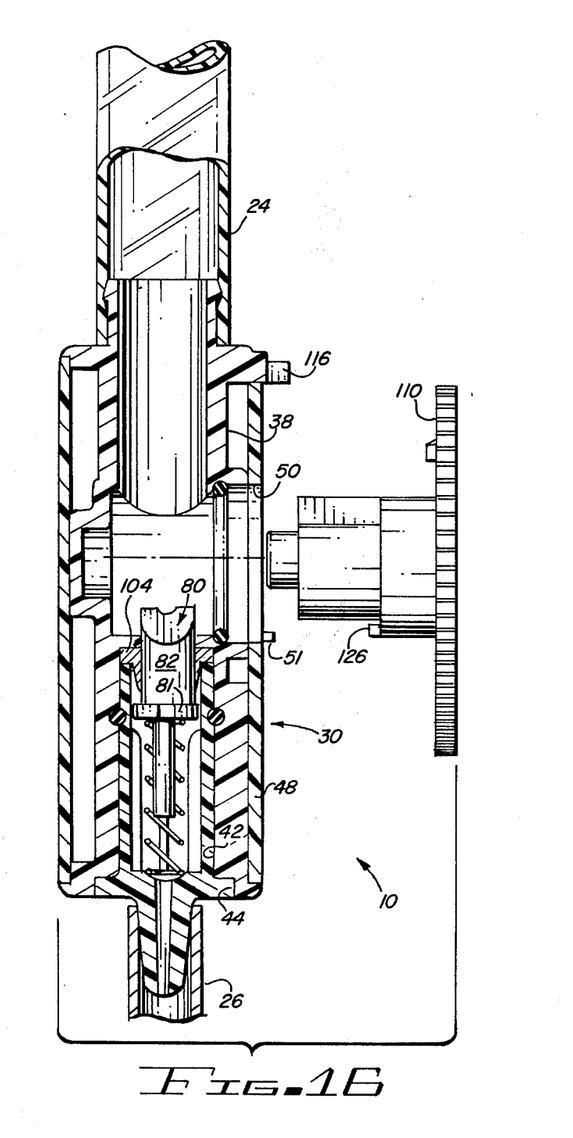
FIG. 16 is a sectional view of the device.

The control device of the present invention also lends itself to other means for positioning of the metering pin 80 within the valve seat 104 and metering tube 60. For example, FIGS. 10 and 11 show inclusion of a rack and pinion instead of a cam for progressive positioning of the metering pin. In FIGS. 10 and 11, the metering pin 80 is axially moveable within tube 60 by means of a rack and pinion arrangement generally designated by the numeral 130. The structure of the metering pin 80, tube 62 and valve seat 104 which performs the valving or metering function are essentially the same as has been described with previous figures and further detailed description is not deemed necessary with reference to these figures.

The rack and pinion arrangement 130 includes a dial 132 which is mountable at the exterior of the instrument housing. A shaft 136 extends into the flow passageway defined by channel 38. The inner end of shaft 136 carries pinion gear 138. Pinion gear 138 engages teeth 142 of linear rack 144 which extends axially from the upper end of pin 80. A guide channel 146 is spaced apart in parallel relationship with rack 144 and defines slots 148 which receives the periphery of the teeth of gear 126 as the gear rotates. An upper stop member 150 extends transversely between channel 146 and rack 144. It will be obvious that as dial 32 is rotated, motion will be imparted to the metering pin 80 through rack and pinion 134 and 128 and that the metering pin may be selectively positioned relative to valve seat 104 to regulate or meter flow as has been described.

FIGS. 12 and 13 show still another arrangement for axial advancement and retraction of pin 80. The embodiment shown in FIGS. 12 and 13 is generally designated by the numeral 160 and includes a dial 162 mounted for rotation in the housing of the device. A shaft 164 extends into the flow passageway of channel 38. The inner end of shaft 164 carries small diameter gear 166 which, in turn, drives larger gear 168. Gear 168 is mounted on shaft 170. Gear 172 is mounted on common shaft 170 with gear 168. Gear 172 is in engagement with teeth 176 of linear rack 174. A stop 178 extends from the upper end of rack 174. The gear train comprising gear 166, gear 168, gear 172 and rack 174 serves as a reduction system to provide more precise positioning of the metering pin. One complete revolution of gear 166 will impart only a partial revolution to gear 170 based on the ratio of the number of teeth between gears 168 and 166 which is translated to axial movement of pin 80 by rack 174. As mentioned above, the gear reduction system provides for a more precise positioning of the metering pin as is required.

Still another means of positioning the metering pin 80 is shown in FIGS. 14 and 15. In these figures, the instrument housing 180 has a face plate 172 provided with an axial slot 184. An actuating lever 185 extends through slot 184 and is pivotally mounted within the housing at pivot point 188. An indicator 186 on the outer end of lever 185 cooperates within indicia along slot 184. The inner end of lever 185 is attached to plunger 190 connected to metering pin 80. The position of pivot point 188 is displaced toward plungger 190 so that linear movement of indicator 186 results in a small proportional movement at plunger 184. This results in preciseness of setting and permits the attendant to more accurately position the metering pin.

In the description of the embodiments shown in FIGS. 9 to 15, certain details have been omitted for purposes of clarity. It is understood that metering pin and cooperating valve seat are as have been described with reference to previous figures.

Figures 17, 18:
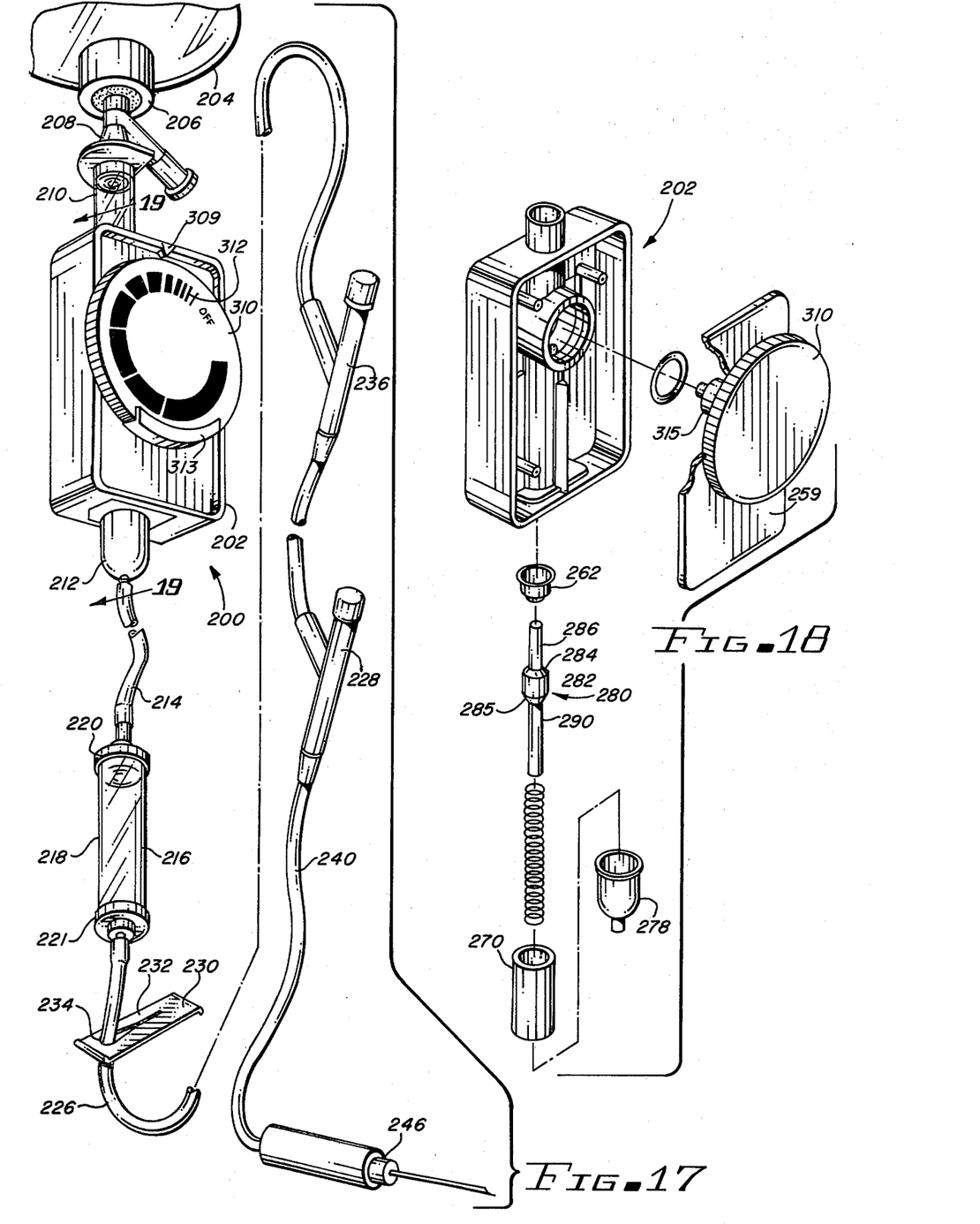
FIG. 17 illustrates another embodiment of the present invention connected in a complete IV system with multiple injection sites.
FIG. 18 is an exploded view showing the details of the flow regulating device shown in FIG. 17.

Another embodiment of the present invention is illustrated in FIGS. 17 to 21, generally designated by the numeral 200. As shown in FIG. 17, embodiment 200 includes flow control device 202 connected in an IV system including a bottle or container 204 of an appropriate IV solution. Bottle 204 terminates at a puncturable outlet 206 which is sealed by a plug or stopper. A piercing spike 208 is inserted through the stopper and is connected to the flow control valve 202 by transparent, cylindrical drip chamber 210. The outlet of control valve 202 is connected by nipple 212 and tubing section 214 to lower drip chamber 216. Lower drip chamber 216 consists of a cylindrical flexible, transparent tube 218 having caps 220 and 221 at the opposite ends of the tube 218. The lower cap 221 is connected to tubing section 226 about which is positioned a slide clamp 230. Clamp 230 consists of a generally flat plate 232 defining a slot 234 therein. The slot 234 is shown as generally tear-drop shape converging at one end so that the tube may be totally or partially closed by engagement along the slot. The lower end of tubing section 226 is connected to a Y-injection fitting 236. A second Y-injection site 238 may be interposed in the system below Y-injection site 236. Lower tubing section 240 terminates at administration needle 246.

Figure 19:
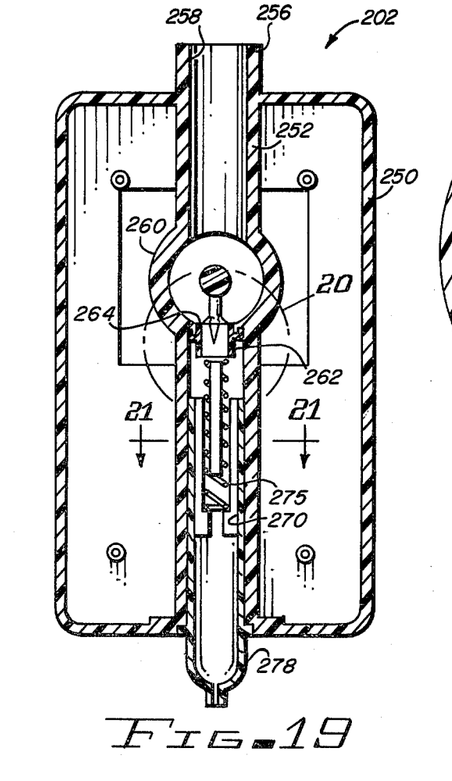
FIG. 19 is a sectional view of the device shown in FIG. 18.
Figure 21:
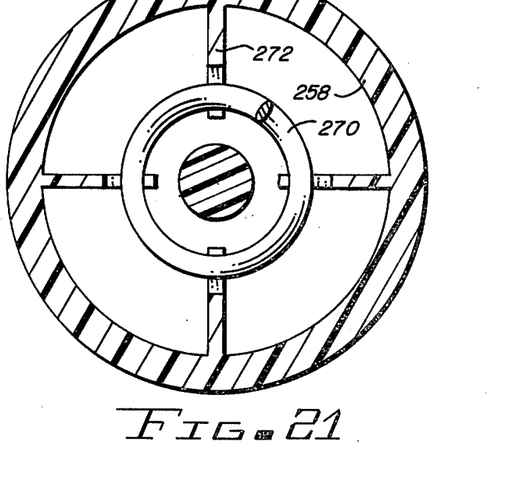
FIG. 21 is a sectional view taken along lines 21—21 of FIG. 19.

The construction of the flow control valve 202 is best shown in FIGS. 18, 19 and 21. Control device 202 includes generally rectangular body or housing 250. A channel 256 extends axially through body 250 defining a flow channel 258. Drip chamber 210 is connectable at the upper extension of flow channel 256 which forms a coupling. An annular hub 260 intercepts channel 256 dividing the channel into upper and lower sections. A cover plate 259, as best seen in FIGS. 17 and 18, is engageable over the front face of the body. A cylindrical valve seat 262 is positioned at opening 264 where hub 260 intercepts the lower portions of passageway 258. Cylindrical guide tube 270 is positioned within lower passageway. Guide tube 270 has a plurality of radially inwardly extending projections 272 which receive an axially extending compression spring 275. Nipple 278 extends from the lower end of the passageway.

Metering or control of flow is achieved by axial displacement of metering pin 280 relative to the valve seat 264. Metering pin 280 has a generally cylindrical body portion 282 which converges or tapers at its upper end at 284 to axially extending projection 286 which serves as a cam follower. The lower end of body 282 tapers at 285 inwardly to axially extending guide pin 280 which is received within spring 275 and biased upwardly thereby.

A metering notch 300 extends axially in the cylindrical service of the body portion 282. Notch 300 may be of various cross-sectional shapes but is shown as V-shaped decreasing in width and depth axially proceeding downward. Circular dial 310 is provided with indicia 312 and secured in place by an annular lip 313. A cam 315 is rotatable within annular hub 260 by means of dial 310. Cam 315 is substantially as has been described with reference to FIGS. 3 and 4 and is generally spiral in configuration engaging cam follower 286 of the metering pin 280.

Figure 20A:
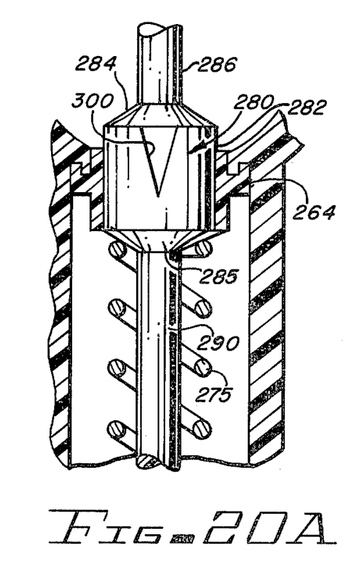
FIGS. 20A to 20C are enlarged detail views illustrating various positions of the metering pin as indicated in FIG. 19.
Figure 20B:
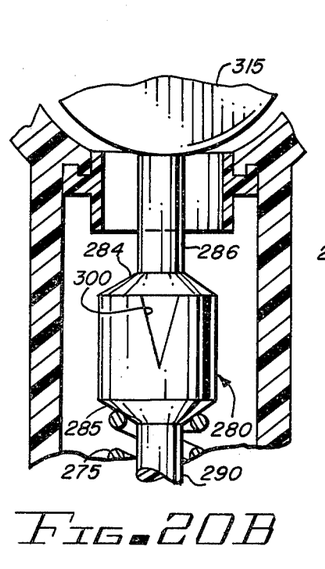
Figure 20C:
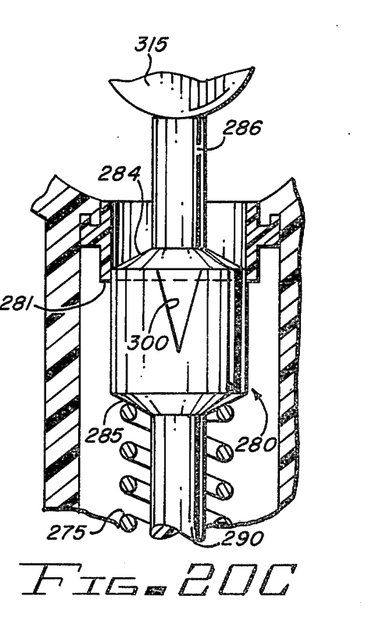

FIGS. 20A, 20B, and 20C illustrate the relative position of the metering pin 280 in various operating positions. In the position shown in FIGS. 20A, seat 264 engages body 282 of metering pin 280 and blocks flow through the lower flow passage. In FIG. 20B, cam 315 has been rotated to displace the metering pin downwardly a sufficient distance so body 212 is positioned below the lower edge of seat 264 to allow purge or full-flow into the lower passage.

With cam 315 rotated to the position shown in FIG. 20C, the lower edge 281 of the valve seat 264 axially registers along the metering groove 300 and progressive, infinite regulation of the flow rate from the purge occurs in this regime. As the horizontal cross-sectional area of the flow notch 300 at edge 281 decreases, the flow correspondingly decreased.

Referring to FIG. 17, the system utilizing the upper drip chamber 210 and lower drip chamber 216, including the unique IV flow control valve is used as follows. The appropriate bottle of solution is selected and preferably suspended from a hanger in conventional fashion. The flow control valve 202 is set so that a location on indicia 312 is aligned with marker 209 in a full-flow position. Slide clamp 230 is moved to completely pinch-off tubing 226. The spike or piercer 280 is inserted into the outlet of the solution container 204 which may be a bottle or bag. The bottle or bag is suspended from the IV stand and the attendant next squeezes the lower drip chamber 216 until fluid appears in the upper drip chamber and the chamber is approximately one-half full. Needle 246 is secured to the end of tubing section 240. Slide clamp 230 is released which allows the solution to clear all air in the tubing and needle. Inverting and tapping Y-injection sites 236 and 238 freeing the trap of air is also recommended. When all air is cleared from the tubing needle, dial 310 is turned to the off-position. When the vena puncture is completed and the line connected to the patient, the attendant sets the established flow rate by rotating dial 310 to the desired location. The recommended procedure is to time the flow rate for one minute to confirm that the rate is correct.

For a change-over or a transfer to a new container, first, either turn the dial 310 to the position or close the slide clamp 230. Flow should be suspended prior to removing the container and dial from the IV stand.

The system described above may be used with the embodiment of the valve described in the preceeding figures. The advantage of the entire system 200 including the flow control valve 202 insures that air is completely purged from the system.

Figure 22:
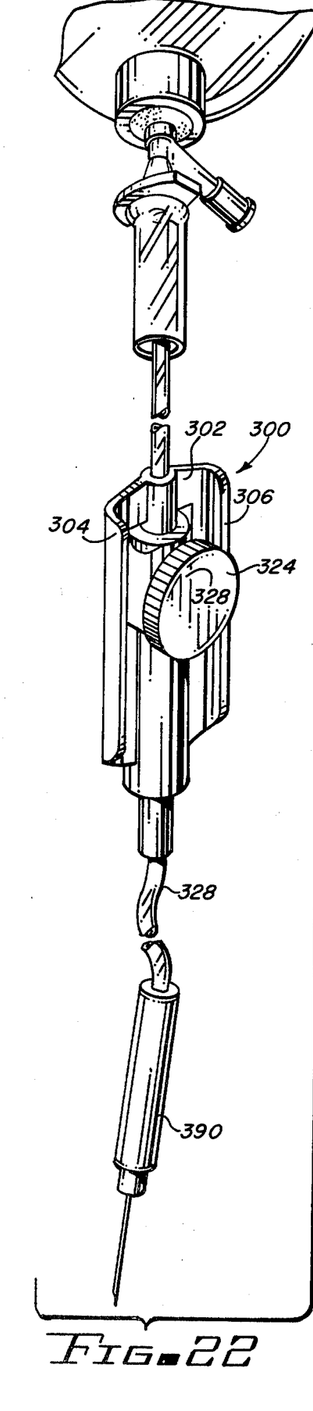
FIG. 22 is a view showing an IV system including still another embodiment of the flow regulating device of the present invention.
Figure 23:
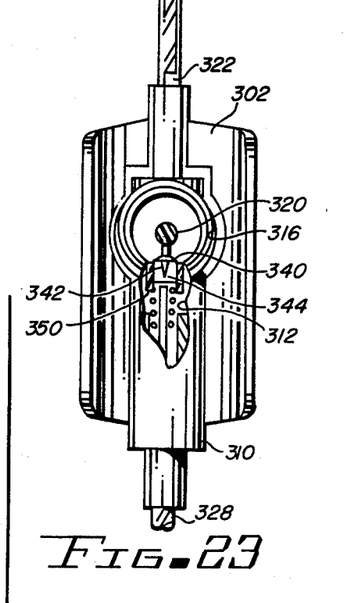
FIG. 23 is a plan view of the device shown in FIG. 22 partly broken away.
Figure 24:
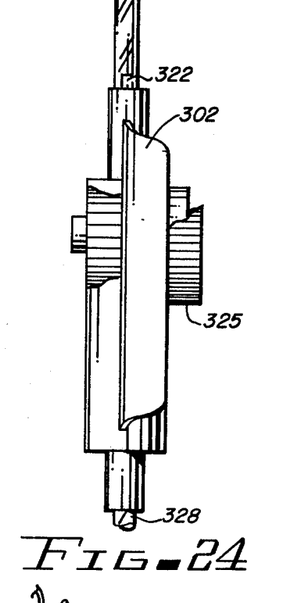
FIG. 24 is a side view.

FIGS. 22, 23 and 24 illustrate still another embodiment of the present invention which is generally designated by the number 300. Flow control or metering valve 300 is generally designated an "in-line" flow controller including a planar body 302 having upwardly turned flanges 304 and 306 at the outer longitudinal edges of the body 302. Cylindrical channel 310 is integrally formed as part of body 302 and defines an interior flow passage 312. Flow passage 312 is intercepted at annular bore 316 to rotatively receive cam 320. Cam 320 has a generally spiral configuration as has been previously described and is connected to a dial 325 which may carry appropriate indicia 328 for indicating the position of cam and the corresponding flow rate.

Flow passage 312 has upper and lower fittings 322 and 328 for connection to appropriate tubing sections. As best seen in FIG. 23, metering pin 340 is axially displaceable in passage 312 by cam 320. Pin 340 is generally configured as has been described with reference to FIGS. 19 and 20 and is provided with a variable area of flow notch 342 in body 344. The body 344 of pin 340 can be relatively positioned with reference to valve seat 350 to control flow through the flow passageway. In other respects, the flow control valve 300 operates generally as has been described with reference to previous figures.

Figure 25:
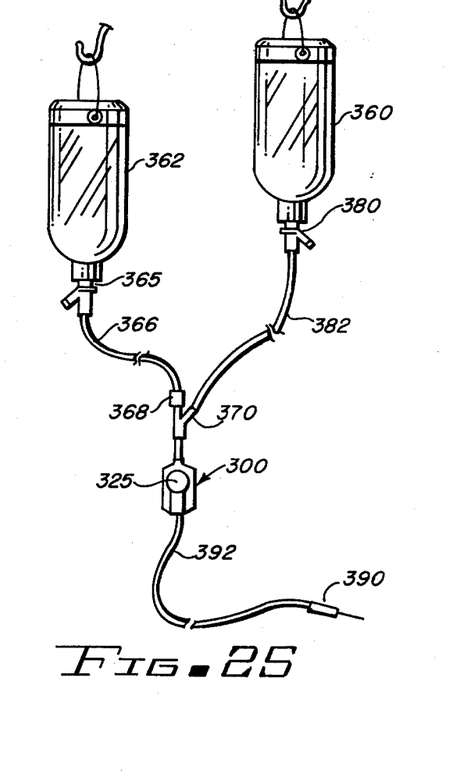
FIG. 25 illustrates the device is a multiple IV bottle system.

In FIG. 25, flow control valve 300 is shown in a multiple set system having secondary fluid container 360 and primary fluid container 362. Piercing spike 365 is connected to container 362 and is connected via hose 366 to ball check valve 368 as the type known in the IV therapy art. Ball check valve 368 is, in turn, connected to one of the inlet ports of Y-connector 370. Secondary bottle 360 is shown elevated above primary bottle container 362 and is connected by spike 380, tubing section 382 to the other inlet 384 of Y-connector 370. The outlet of Y-connector 370 is connected to an administration needle 390 by tubing section 392.

In the system shown in FIG. 23, flow controller 300 is shown in an in-line position below the Y-connector in tubing section 392. Flow controller 300 can be purged by inverting the flow controller and striking the flow controller sharply with the dial 325 in a full-flow position. This will cause the trapped air to be discharged as flow is initiated. Once the administration has begun, the secondary bottle or container 360 will empty with the ball check 368 preventing fluid from being discharged from container 362. When the container 360 reaches a pre-determined level, ball check will open allowing the contents of the primary solution bottle 362 to discharge. This arrangement prevents entrapment of air in the IV system with an automatic transfer from the secondary container 360 to the primary container 362.

The multiple set or "piggyback" system described with reference to FIG. 23 has particular advantage when feeding several solutions or may also be used to provide several containers of the same solution so a patient can be administered an IV solution for a longer period without a requirement of the nurse having to change solution containers. The start-up procedure is also simplified and purging the system of air is convenient since the valve 300 is in-line. This allows the attendant to easily invert the valve 300 for removal of any trapped air. The in-line system of FIGS. 22-25 is compatible with most conventional IV systems as it is capable of connection by a taper-lock or similar coupling at a suitable location.

It will be obvious to those skilled in the art that other means may be used to advance and retract the metering pin within the valve to perform the metering function. For example, it is possible to utilize engageable threaded members which may be rotated to result in relative axial movement of the metering pin to the valve seat.

The IV control valve of the present invention can be inexpensively manufactured of any suitable materials such as ABS or similar plastic materials. Because of the simplicity of construction and the relative small number of parts, the device can be designed as a disposable unit. The device would be preferably autoclaved or gas sterilized and provided to the ultimate user in a sterilized package for attachment in an IV system. When IV administration is complete, the entire unit including the drip chamber, control device, administration tip and tube can be disposed of to minimize cross-contamination and for efficient labor saving practice. The device of the present invention preferably can be manufactured in a compact size such that the unit can be grasped in one hand by the attendant. The dial member being relatively large and preferably extending beyond the lateral sides of the instrument housing facilitates operation in one hand. This allows the attendant to make any necessary adjustments with one hand and, as an independent check of flow rates, to easily time flow rates by reading a wrist watch or other timing instrument held or worn on the other hand.

Accordingly, from the foregoing, it is understood that accurately and highly predictable and repeatable flow rates can be achieved by positioning the metering pin with respect to the valve seat to vary the flow area through the valve.

The invention may be embodied in other specific forms without departing from the spirit and scope of the present invention. It will be obvious to those skilled in the art to make various changes and modifications to the embodiments described herein without departing from the spirit and essential characteristics of the invention. To the extent that these changes, alterations and modifications do not depart from the spirit and scope of the appended claims they are intended to be encompassed therein.

I claim:

1. An IV system for accurately establishing and maintaining pre-determined administration flow rates between a purge and "off" position from a source of fluid having a puncturable seal, said system comprising:
   (a) a flow metering valve including:
      (i) a housing defining a fluid passageway having opposite upper and lower ends, said passageway including a valving surface;
      (ii) a metering member having a body axially moveable relative to said valving surface, said metering member defining a flow metering notch in one surface, said notch having a cross-sectional area which varies axially along said member for metering flow therealong, said metering member further defining a flow passageway for establishing a purge position, said metering member having a first closed position with said body blocking flow at said valving surface, a second purge position with flow across said valving surface at said flow passageway and a third metering position with flow across said valving surface through said notch, said second purge position establishing a greater flow rate than said third metering position;
      (iii) actuating means cooperative with said metering member to axially progressively displace said member relative to said valving surface to establish continuous and infinite flow metering along said notch portion of said flow passage in said third position whereby the user can establish a pre-determined flow rate;
   (b) an upper drip chamber connected to said upper end having piercing means for puncturing said seal;
   (c) a lower drip chamber connected to the said lower end of said passageway;
   (d) tubing connected to said lower drip chamber terminating at connector means adapted to receive administration means; and
   (e) clamp means associated with said tubing.

2. The system of claim 1 further including at least one Y-connector interposed between said drip chamber and administration means.

3. An IV system for accurately establishing and maintaining pre-determined administration flow rates between a purge and "off" position from a source of fluid, said system comprising:
   (a) an in-line flow metering valve including:
      (i) a housing defining a fluid passageway having opposite upper and lower ends, said passageway including a valving surface;
      (ii) a metering member having a body axially moveable relative to said valving surface, said metering member defining a flow metering notch in one surface, said notch having a cross-sectional area which varies axially along said member for metering flow therealong, said metering member further defining a flow passageway for establishing a purge position, said metering member having a first closed position with said body blocking flow at said valving surface, a second purge position with flow across said valving surface at said flow passageway and a third metering position with flow across said valving surface through said notch, said second purge position establishing a greater flow rate than said third metering position;
      (iii) actuating means cooperative with said metering member to axially progressively displace said member relative to said valving surface to establish continuous and infinite flow metering along said notch portion of said flow passage in said third position whereby the user can establish a pre-determined flow rate;

(b) a drip chamber;

(c) means connecting said drip chamber to said source of fluid;

(d) first flexible tubing means interconnecting said upper passageway to said drip chamber whereby said valve may be purged by inverting said valve; and (e) second flexible tubing means connected to said lower passageway and terminating at administration means.

4. The system of claim 3 including at least one Y-connector interposed between said valve and said source of fluid.

5. The system of claim 4 wherein said Y-connector includes check valve means and further including a second fluid source connected to said Y-connector establishing a "piggyback" arrangement.

6. A metering device for accurately establishing and maintaining predetermined flow rates between a purge and flow blocking positions in an IV system including a source of parenteral or IV fluid and a fluid delivery system, said metering device comprising:

(a) a housing defining a fluid passageway having opposite ends, one end connectable to said fluid source and the other end connectable to said delivery system, said passageway including a valving surface;

(b) a metering member having a body axially moveable relative to said valving surface, said metering member defining a flow metering notch in one surface, said notch having a cross-sectional area which varies axially along said member for metering flow therealong, said metering member further defining a flow passageway for establishing a purge position, said metering member having a first closed position with said body blocking flow at said valving surface, a second purge position with flow across said valving surface at said flow passageway and a third metering position with flow across said valving surface through said notch, said second purge position establishing a greater flow rate than said third metering position;

(c) actuating means cooperative with said metering member to axially progressively displace said member relative to said valving surface to establish continuous and infinite flow metering along said notch portion of said passage in said third position whereby the user can establish a predetermined flow rate.

7. A metering device for accurately setting flow rates in an IV system including a source of IV or parenteral fluid, said valve comprising:

(a) a housing having a generally planar back with opposite longitudinal sides and flanges at said sides to facilitate grasping by the user;

(b) a fluid passageway within said housing;

(c) a valve seat in said passageway having a valving surface;

(d) a generally cylindrical metering member axially moveable relative to said valve seat, said metering member including a cam follower and said member further defining a flow passage in a surface having a cross-sectional area which varies axially along at least a section of said flow passage;

(e) actuating cam means having a generally spiral cam surface cooperable with said cam follower;

(f) biasing means urging said metering member into engagement with said cam surface in a direction to reduce flow; and (g) dial means moveable relative to said housing for imparting rotational movement to said actuating cam means whereby said cam surface axially displaces said member relative to said valving seat surface to progressively regulate flow from a closed to a purge position with flow metering occurring along said portion of said flow passage which varies in cross-sectional area.

* * * * *